United States Patent [19]

Toft et al.

[11] Patent Number: 5,407,436

[45] Date of Patent: Apr. 18, 1995

[54] SYRINGE WITH RETRACTABLE NEEDLE

[75] Inventors: John F. Toft, Cheshire; Peter Jeffrey, Liverpool, both of England

[73] Assignee: Safe-T-Limited of Laurel House, Lonan, Isle of Man

[21] Appl. No.: 129,120

[22] PCT Filed: Apr. 10, 1992

[86] PCT No.: PCT/GB92/00652

§ 371 Date: Oct. 12, 1993

§ 102(e) Date: Oct. 12, 1993

[87] PCT Pub. No.: WO92/18187

PCT Pub. Date: Oct. 29, 1992

[30] Foreign Application Priority Data

Apr. 11, 1991 [GB] United Kingdom ............... 9107647

[51] Int. Cl.⁶ .............................................. A61M 5/00
[52] U.S. Cl. ..................................... 604/195; 604/110
[58] Field of Search ............... 604/195, 110, 187, 220, 604/225, 218, 263

[56] References Cited

U.S. PATENT DOCUMENTS

| | | | |
|---|---|---|---|
| 772,114 | 10/1904 | Pappenheim | 604/220 |
| 2,037,768 | 4/1936 | Dickenson | 604/225 |
| 4,838,869 | 6/1989 | Allard . | |
| 4,994,034 | 2/1991 | Botich et al. . | |
| 5,049,133 | 9/1991 | Pascual . | |
| 5,211,629 | 5/1993 | Pressly et al. | 604/195 |

FOREIGN PATENT DOCUMENTS 669910 4/1989 Switzerland .
WO9007948 7/1990 WIPO .

*Primary Examiner*—John D. Yasko
*Attorney, Agent, or Firm*—Banner, Birch, McKie & Beckett

[57] ABSTRACT

Hypodermic syringe or medical sampler has a hollow needle (115) that is automatically retractable after use. A one-piece body (101) moulding has a main chamber for a plunger (105) or sampler container or drug cartridge, a forward chamber (111) to house a spring (133) to bias a needle holder (117), and internal latching formations (141) to retain the needle holder (117) with the spring (133) compressed in the forward chamber until automatic retraction when the latching formations (141) are released by end of plunger movement. Direct plunger-to-body sealing involves an over-size plunger head (105 H) forcing head and wall deformation. Both ends of the spring (133) have seals (119, 160) for the forward chamber (111). The needle, its holder, spring and seals can be installed using a sliding guide. Pressure testing can be combined with needle lubrication, and retraction prevention with sterilising tell-tale. The plunger (105) has top and grip formations (105 F) for the needle holder (117), and the needle can be double ended for taking samples or emptying drug cartridges.

25 Claims, 6 Drawing Sheets

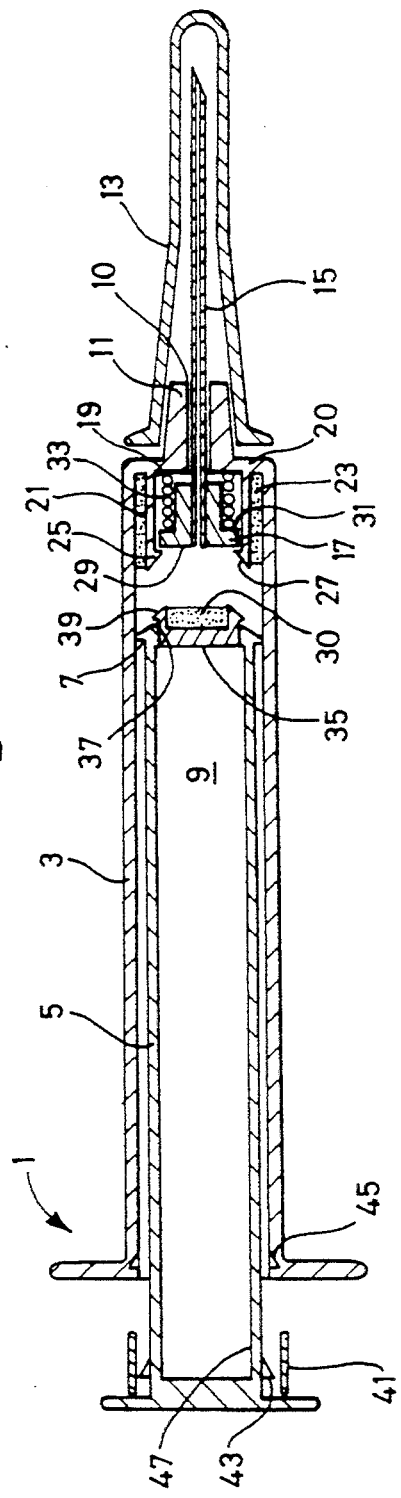
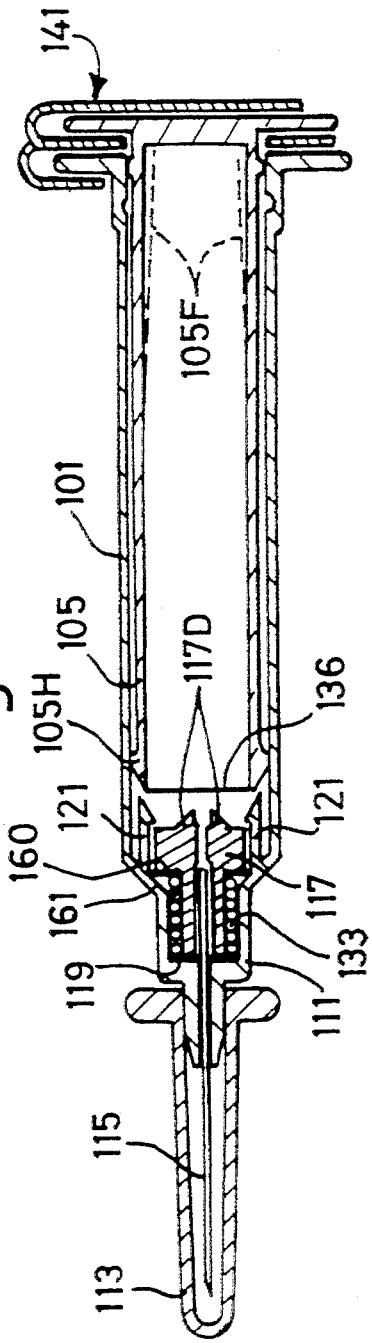
Fig. 1
Fig. 2

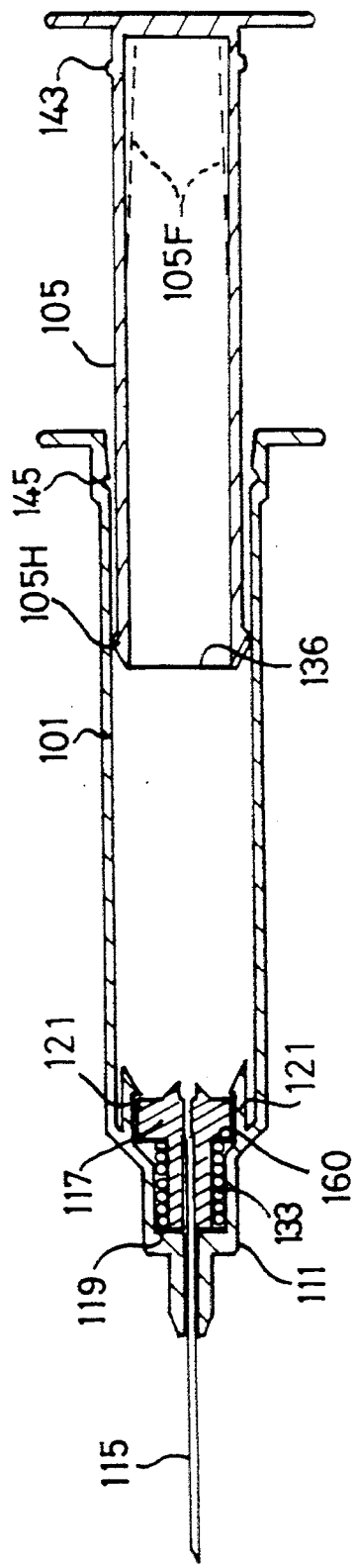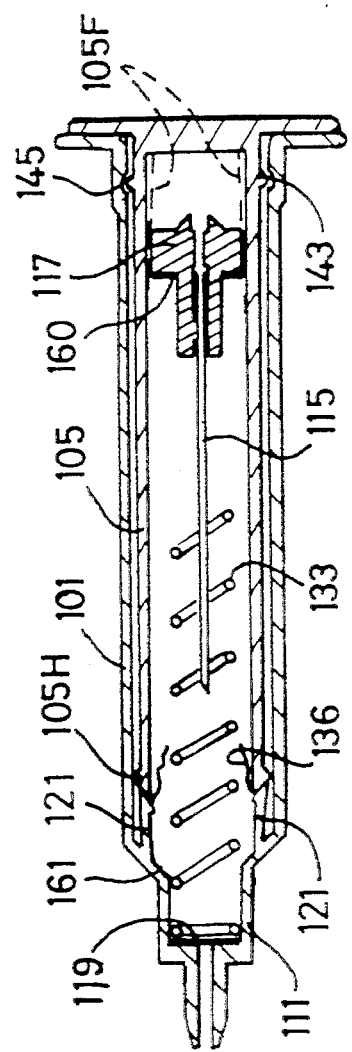

SYRINGE WITH RETRACTABLE NEEDLE

DESCRIPTION

The present invention relates to protection against accidental skin piercing by needles of used hypodermic syringes or medical samplers, or the like.

A used such needle poses a health hazard and considerable attention has been directed to reducing the hazard by disposal regimes and means of sheathing the needle tip after use. Also, numerous proposals have been made for automatic retraction of a needle after one use, but to date no-one appears to have put forward a practical proposal that is reliable and commercially viable to make, certainly not so that production costs are reasonable compared with the costs of existing products without needle retraction.

The present invention aims to improve practicality and viability in providing for reliable automatic needle retraction.

It is standard for a syringe or sampler construction to include a hollow cylindrical body, a plunger slidable in the body, and a seal between the plunger and the body effective during sliding of the plunger to express syringe or sampler contents and/or to draw them in before sample expression. Hitherto, acceptedly satisfactory seals have been expensive items made of rubber.

According to one aspect of this invention, there is provided a hypodermic syringe or sampler body and slidable plunger construction that permits direct sealing between the plunger and the body, at least for operation only once but including a number of movements at least for initial entry, retraction to load, and pressing down to express. A suitable construction comprises a hollow cylindrical body, preferably circular cylindrical, and a plunger having at least a hollow head with a continuous outer rim to engage the body internally when slid therein; the plunger head rim, as made, being nominally of greater external size than internal size of the body, but being radially inwardly deformable by the body when slid therein, preferably with some temporary radially outward deformation of the body itself as the plunger head travels along the interior surface of the body.

Satisfactory mouldable synthetic plastics materials for the plunger head, preferably the entire plunger, and the body, can have different resistances to deformation, typically less resistance for the plunger head and more resistance for the body, at least for both as made. Inherently softer or more deformable and harder or less deformable materials for the plunger and the body, respectively, include, for the body, polypropylene, preferably nucleated (at least 0.2% preferably 0.3–0.35%) polypropylene having good clarity/transparency, strength and resistance to shrinkage/warpage during moulding (homopolymer having proved promising in prototypes); and, for the plunger, polyethylene, preferably high-density to give good seal performance and stability (Melt 7 having proved promising in prototypes). At least for such specified materials, the difference in nominal diameters of body interior and plunger head exterior can be up to 50 microns or more, preferably at least 25 microns.

Direct sealing between such a plunger head and body that is satisfactory for intended single use of a hypodermic syringe or sampler eliminates separately made and hitherto relatively expensive seal provisions.

A large number of generally impractical or uncommercial prior proposals for hypodermic syringes with automatic needle retraction after use have been considered. They typically require the hollow needle to be fixed to a holder, commonly called a 'hub', and for such hub to be acted upon by a compression spring and by releasable detent or trigger means to release spring action and forcibly send the needle and its holder into the interior of the syringe or sampler, often into the plunger which will be hollow at least for that purpose. Generally, however, such provisions, including detent or trigger means, involve or are involved in an assembly attachable to the forward end of the syringe or sampler body and/or plunger, and/or in a part or parts fitted interiorly of the body, whether to the body or to the plunger or to both. Such provisions tend to be costly in themselves and in terms of assembly.

According to another aspect of this invention, a syringe or sampler body is made as a one-piece moulding complete with a main elongate cylindrical chamber to take a plunger slidably, a forward or extension chamber beyond end of plunger movement to house a spring and a holder for a hollow needle capable of passing through that forward or extension chamber, and internal integral latching formations for the needle holder to retain it with the spring compressed in the forward or extension chamber and acting on the needle holder.

Preferred latching formations extend in the main chamber generally axially of the body to free ends having radially inwardly directed retaining formations, and are deflectable radially outwardly at their free ends both for release from a moulding tool, and for latching and release of the needle holder, say (and further preferably) when directly engaged by said plunger. It is particularly advantageous for such latching formations to have substantially no deflection from axial parallelism with the body when in latching engagement with the needle holder.

A particularly convenient and advantageous one-piece body moulding has its forward or extension chamber of reduced sectional size compared with its main chamber (both preferably circular), and its latching formations extending internally substantially outward of registration with walling of the forward or extension chamber and further preferably evenly spaced about the axis of the needle. Preferably, each of the latching formations is at least partially within a respective one of localised outward formations of the main chamber adjacent the forward or extension chamber.

Compared with known prior proposals for hypodermic syringes with automatic needle retraction, a one-piece mouldable body part of the second-mentioned aspect of this invention represents substantial cost saving. This cost saving is increased when taken in conjunction with the first-mentioned aspect of this invention in further avoiding an expensive plunger-to-body seal. However, the one-piece body aspect is viable with a piston that has a plunger head-to-body seal, particularly of much smaller size (typically a simple small 'O' ring) than customary in practice hitherto.

Use of a syringe or sampler body having a cylindrical main chamber for a plunger and a forward or extension chamber of reduced section extending therefrom for a needle retraction drive system is also capable of exploitation to greatly aid assembly in accordance with a further aspect of this invention. In this further aspect, a needle and immediately related retraction drive parts are placed in a guide that is slidable into the main chamber along its side walling to take the needle and its retraction drive parts up to the forward or extension chamber in axial registration therewith for insertion into that forward or extension chamber simply by being pushed off the guide.

Such simple assembly is readily suited to high volume automated production, and represents a significant improvement in assembly costs compared with prior known proposals.

Sealing is, of course, provided so that hypodermic syringe or sampler contents do not escape past the needle (rather than only through it), preferably with isolation also from needle retraction drive parts at least to save wastage of contents that would not be expressible from such a position, and a further aspect of this invention concerns such sealing.

That further aspect itself has, in reality, two aspects, namely use of a septum disc that is uninterrupted save for being pierced by the needle, whose passage therethrough can readily be assisted by application of lubricants, say at first piercing and/or afterwards (before sterilising) for retraction; and use of a sealing washer on a needle holder to seal between a main plunger chamber of a syringe or sampler body and a or said forward or extension chamber housing the needle and retraction drive parts before the syringe or sampler is used.

Lubrication may be by application of silicone material to the septum disc and/or the needle at first piercing, normally centrally and readily jigged up separately from use of a guide as in the third-mentioned aspect, and afterwards to aid forced retraction. Needle holder sealing can be below a head of the holder or hub and even be aided by action of the latching means on the opposite side of the head.

Where, as is preferred, the plunger is hollow and serves to receive the retracted needle and associated retraction drive parts, such as spring and seals, it can be closed off by a thin rupturable disc or membrane that is subsequently ruptured by the rear end of the needle, or the needle holder (as is preferred using appropriate formations on its innermost end). Such disc or membrane may well be such as not to rupture when subjected only to maximum retraction spring force, i.e. so the plunger needs to continue to be pressed down at or even after the full effective expression stroke and spreading of latching provisions to release the needle and its holder. However, a disc or membrane that does rupture easily when subjected to the spring bias force is preferred.

Where the plunger has a deformable head rim that is compressed inwardly by the body for sealing purposes, the rupturable disc or membrane could be inward of the end of the plunger and its head rim, but by an amount less than the intrusion of the needle or its holder into the plunger accommodating chamber of the body. However, it is preferred to use a pre-tensioned membrane or film that is stretched before application to an extent beyond any compression effects on and from the plunger head rim in the body, i.e. to remain taut or at least not become slack. A satisfactory disc or membrane can be ultrasonically welded or heat welded (say impulse heat welded) or solvent welded in place in a suitable jig. Suitable adhesives represent another alternative.

Deploying all of the above aspects and preferences of this invention together results in a hypodermic syringe set having no more than eight parts, namely one-piece body with integral latching formations, a plunger, rupturable plunger end disc or membrane (if not integrally formed with the plunger), a needle, a needle holder or hub, a septum disc, a spring, and a needle holder or hub seal. Moreover, those parts are extremely easily assembled, and can meet all sealing, force and sterilisation requirements applied at least in the United Kingdom and by the World Health Organisation. Savings from omitting conventional large rubber plunger-to-body seals, and from easy assembly, enable a hypodermic syringe to be made economically, feasibly matching, even beating, manufacturing costs of conventional hypodermic syringes, certainly beating costs and likely performance for all prior retractable needle proposals we have seen to date.

It is desirable and preferred that a plunger receiving a forcibly retracted needle and retraction drive parts be trapped in the body when in that state, but be reasonably effectively prevented from reaching that state until after first use. Achieving same constitutes a fifth aspect of this invention when done by way of a spacer between the free end of the plunger and the corresponding end of the body, to avoid snap-in of complementary body and plunger formations. A preferred spacer has a part or parts that can temporarily latch to the body end and/or the plunger end, and further preferably has incorporated therein indication of sterilising have taken place, say as normally done by irradiation.

A suitable spacer can be of sheet form apertured to fit over the plunger stem and tearable for removal. A preferred sheet is of thick paper or cardboard and carries a spot or printing of radiation indicating type, say ink that changes colour. Tear perforations can be pre-formed, say at a return bend for the sheet to pass twice about the plunger stem beneath its head. One or each end of the sheet can be preformed with a fold that provides either or both of folding over an end flange of the body and the free end of the plunger.

It is also considered preferred and advantageous herein for lubrication of the needle to be done, or to be capable of being done, in a test operation, say using a blind cup with a septum disc closure carrying silicone and penetrated by the needle for prescribed pressure to be applied to the plunger for test purposes.

It will be appreciated that use as a sampler, i.e. for taking in patients' samples from veins etc (through the needle) is as feasible as a hypodermic syringe, then with needle retraction after expressing the sample. A double-ended needle can also allow use with pre-loaded drug capsules or cartridges. In both cases, a container (for blood etc sample or with drug etc) will be inserted into a body hereof instead of said plunger, and will have an end-seal that is broken or penetrated by the inner end of the double-ended needle. After loading or unloading the container and removing it from the body, said plunger can be reinserted into the body in order to operate the latching provisions and take the needle etc into its hollow interior. Such a plunger will not need, and preferably will not have, either of a seal to the body or a rupturable closure of its end. Indeed, such a plunger, i.e. not for hypodermic syringe use and action, will preferably be clearly distinguished, say by colour.

It is further envisaged and preferred herein, and can be seen as a yet further aspect of invention, for there to be simple but effective positive retention of a retracted needle in the plunger interior, particularly by way of integrally mouldable and moulded internal formations. Specifically, the plunger can have interior effective capture formations that may be as simple as progressively tapered formations, such as fins, ribs or even flats. Such tapered formations will effectively grip thus slow and stop a hub or holder of the retracting needle and can be located so that a double-ended needle will not reach and penetrate outside the plunger.

Specific implementation for this invention will now be described, by way of example, with reference to the accompanying diagrammatic drawings, in which FIG. 1 is a longitudinal section through one embodiment;

FIGS. 2, 3 and 4 are similar sections showing before, during and after use states of a second embodiment;

FIGS. 5A,B,C are plan, edge-on, and installed views of a preferred spacer of folding sheet type;

FIG. 6 shows a test procedure combined with needle lubrication;

FIGS. 7A,B show assembly of needle retraction drive parts;

FIG. 8 is a detail concerning direct plunger-body sealing:

FIGS. 9A,B are side and head plan views of a needle holder;

Figure 5A:
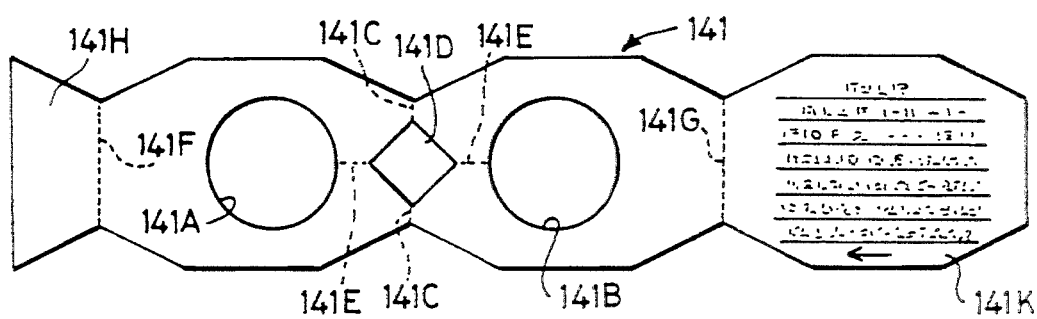
Figure 5B:
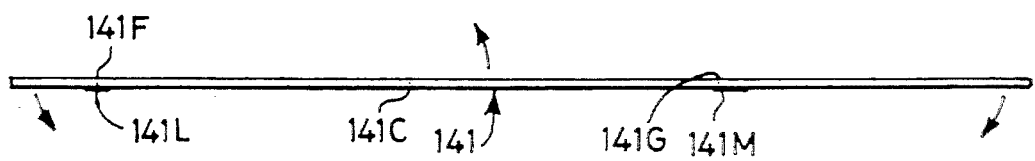

In FIG. 1, a syringe construction comprises a body 1 having a cylindrical bore 3 open to one end to receive slidably within it a hollow plunger 5 shown sealed to the bore 3 by a quite small 'O'-ring 7. The other end of the body 1 has an end wall provided with an axial through-hole 10 in an external axial extension 11 which is frusto-conical to receive a needle sheath 13.

A hollow elongate needle 15 is carried by a holder or hub 17 of top-hat section at its inner end. The needle 15 goes from inside the bore 3, and passes through a septum seal 19 positioned at the inner end 20 of the body 1 and through-hole 10. That end 20 of the body 1 also has extending inwardly therefrom deflectable latch fingers 21 providing latching shoulders 25 and tapered actuating surfaces 27. The fingers 21 will spread radially outwardly when engaged by latch release surface 39 as will be described. An annular space outwardly of the latch fingers 21 is shown filled with a soft rubber infill to occupy space which might otherwise be a source of air pockets. Acting between the end 20 of the body 1, actually seating on the septum seal 19, and an annular surface 31 of the holder or hub 17 is a compression spring 33 shown compressed with the needle 15 latched and held in its extended position by the fingers 21.

The end of the plunger 5 facing the needle 15 is shown closed by a plug 35 that seals relative to the interior of the plunger 5 and has latching fingers 37 engaging the end of the plunger 5. The ends of the fingers 37 are tapered to provide surfaces 39 that cooperate with the tapered faces 27 of the body fingers 21 when the plunger 5 is pushed into the body 1 to its maximum extent. The plug fingers 37 will then also flex radially inwardly, and the space between them is preferably also occupied by a soft rubber infill 30.

Displacement of the plunger 5 into the body 1 is shown hindered by a removable collar 41 disposed about the plunger 5 beyond the opposite end of the body 1. Shown inside the removable collar 41 are teeth 43 on the plunger 5 for engagement in complementary recesses 45 in the adjacent end of the body 1.

In use, as a hypodermic syringe, the needle protection sheath 13 is removed and material drawn into the body 1 in the usual manner by withdrawing the plunger, the required dosage being measured by suitable calibration on the syringe body after expulsion of any entrapped air in the usual manner. The needle 15 is then inserted into the recipient to be injected, and the contents discharged by displacing the plunger 5 down the body 1. There are two possibilities for activating retraction of the needle. One option is for the collar 41 to be removed before commencement of discharge and for the plunger to be moved through the discharge operation until the teeth 39,27 contact and disengage the respective latching fingers 37,21 so that the spring 33 urges the needle 15 to the left in FIG. 1 and the plug 35 moves with the needle 15 into the plunger 5 which, in turn, becomes locked in the body 1 by cooperating engagement of the teeth 43 and recesses 45. Alternatively, the collar can be removed later, after injection use of the hypodermic syringe, and the needle withdrawal from the recipient before final movement of the plunger 5 to trigger retraction of the needle 15.

The materials employed in construction of the plunger can be low friction plastics, and it is readily possible to employ a compression spring 33 that will exert sufficient force to retract the needle 15 from recipient tissue as well as drive it within the plunger 5. A bleed hole 47 near the outer end of the plunger 5 avoids imposing undue restriction on movement of the plug 35 and needle 15 down the plunger 5.

FIGS. 2, 3 and 4 show as-made and sterilised (before packaging or after unpackaging, typically from a blister pack), loaded for injection, and retracted needle states, respectively, for another embodiment of this invention. Reference numerals are generally advanced by one hundred, and differences are now described. Although not so shown in FIG. 4, the septum disc 119 may travel with the needle 115 and take the spring 133 with it into the interior of the plunger 105 at automatic retraction.

Figure 5C:
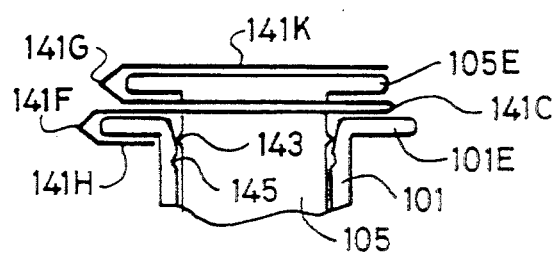

As hindrance to premature needle retraction, the sleeve 41 of FIG. 1 is replaced by an apertured and folded sheet tag 141, which may be of thick paper or card. FIGS. 5A,B,C show more detail including apertures 141A,B both to fit over the plunger 105 below its grippable end 105E when folded at 141C, and at 141D to aid removal by tearing, say aided by perforations at 14E. The doubled thickness between the plunger end 105E and the grippable end 101E of the body 101 prevents engagement of the rib 143 and the groove 145 (shown more rounded than toothing 43 and recessing 45 in FIG. 1 for easier integral moulding and "bumping off" from the mould tools concerned). Folds at 141F,G enable sheet end portions 141H and 141K to engage over flanging of plunger and body ends 105E and 101E. Retention is aided by contact adhesive at 141L,M for edges of the plunger and body end flangings, or, and preferably, holding folds pinched together (not indicated in FIG. 5C for clarity, though fold direction arrows do appear). The top of the sheet end 141K is a convenient place for imprinting or affixing a label carrying any data desired (such as date of manufacture, batch number, manufacturer, syringe capacity, needle size, etc) plus a tell-tale for sterilisation (say an ink that changes colour). The sleeve 41 could, of course, be similarly printed or labelled.

Figure 6:
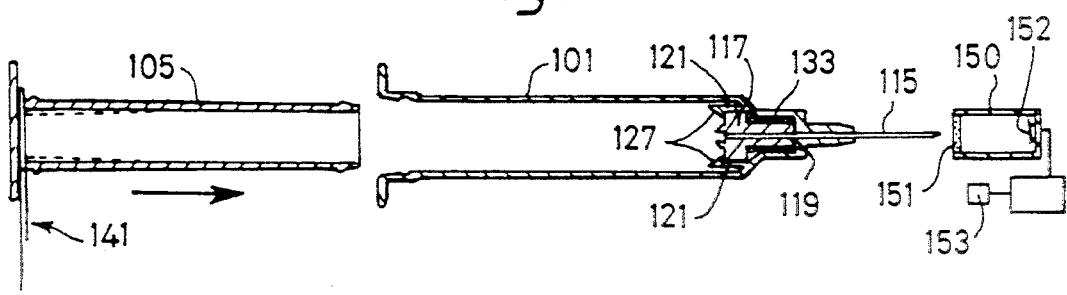

FIG. 6 indicates a combined needle lubrication and test procedure, usually before sterilising but after fitting the tell-tale sheet tag 141, it uses a blind cup type of test cell 150, shown fitted with a rubber septum seal 151, and preferably of a depth capable of taking the whole exposed length of the needle 115 to aid lubrication simply by wiping the septum seal 151 with silicone lubricant. After such full penetration, the plunger 105 is pushed into the body 101, and pressure in the test cell is measured to reach a desired or required value, see sensor 152 and indicator 153. If all is well, the needle sheath 113 will be added and the product sterilised and packaged.

The embodiment of FIGS. 2 to 4 also has a further seal 160 engaged by the opposite end of the spring 133 from the septum seal 119. The seal 160 is of flat washer type and seals to taper 161 by coaction between the needle holder of hub 117 and the latch fingers 121, preferably to cause outer corner deformation of the seal 161 when the latch fingers 121 entrap the holder or hub 117 with the spring compressed in the body extension 111. The seals 119 and 160 both assist retention of contents of the body, but the seal 160 further isolates the body extension 111 and the spring 133 from body contents.

Figure 7A:
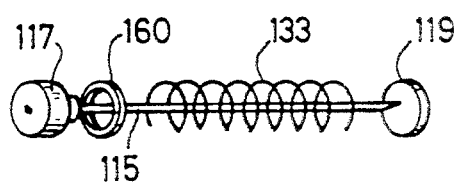
Figure 7B:
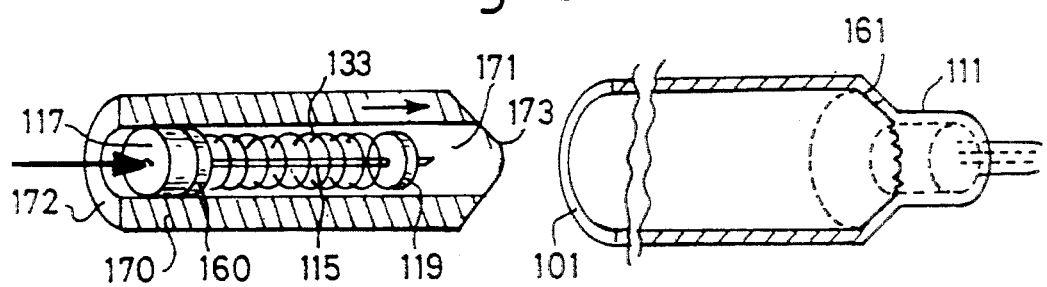

The whole needle and its holder or hub and related drive and seal assembly 115,117,119,133,160 is particularly readily assembled into the body extension chamber 111, see FIGS. 7A,B. In FIG. 7A, the needle 115 is already in the holder or hub 117 and passes through the seal 160 and the spring 133 with its point about to pierce the septum seal disc 119 centrally, as can readily be jigged up. After doing so, the whole is placed in a guide 170 of generally half (or less) cylindrical form with an inner radius or channel 171 matching to the needle holder or hub 117, spring 133 and seals 119,160 and an outer radius presenting a surface 172 matching the interior of the main chamber of the body 101. The thickness of the guide 170 will thus correspond to the difference in diameters between the interior of that main chamber and the interior of the extension 111. It is then a simple matter to slide the loaded guide 170 along the body 101 until its end, or a nose part 173 matching the taper 161 (as shown), can go no further; and for the needle and drive assembly to be pushed off into the then-registering extension 111 until the latch fingers 121 (not shown for clarity) are spread and return to capture the holder or hub 117. If the extension 111 is not central, the latching fingers could be offset too, and the guide 170 match a particular orientation of the body 101 usually with the extension 111 uppermost. That would also involve a plunger requiring orientation. In practice, it is preferable to do no more than offset the needle in the hub or holder 117.

Figure 8:
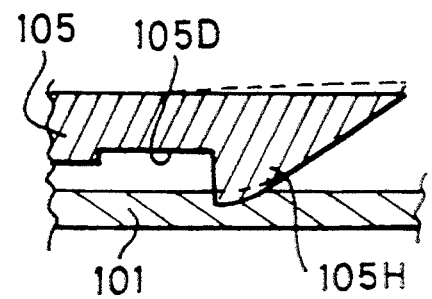

FIGS. 2 to 4 also indicate direct sealing between the plunger 105 and the body 101. An 'O'-ring seal as at 7 in FIG. 1 represents a great saving compared with conventional large rubber mouldings for hypodermic syringes. However, integrally moulding a satisfactory seating that does not require adhesive or other bonding is difficult. Moreover, avoiding any separately made seal part at all represents a yet greater advance and saving. Suitable materials for head 105H of the plunger, actually the whole plunger in a practical integral moulding, and for the body 101, enable that greater advance and saving. A harder, less deformable and advantageously highly transparent material for the body 101 is nucleated homopolymer polypropylene, and a softer, more deformable and satisfactorily sliding and sealing material for the plunger head 105H is high-density Melt 7 polyethylene. Those materials allow a nominal oversize of the plunger head 105H relative to the interior bore of the main chamber of the body 101 of up to 50 microns resulting in small outward deformation of the body 101 as the plunger head slides along it, say as little as 2 microns or less, and a larger compressive inwards deformation of the plunger head 105H. Dashed lines on FIG. 8 give some indications of such deformation (obviously excluding possible volumetric compression at least of the plunger head), but should not be taken as either to scale or accurate, as detail measurement has not been made.

Figure 9A:
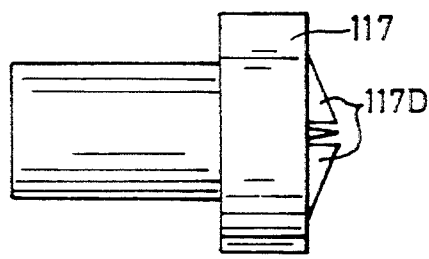
Figure 9B:
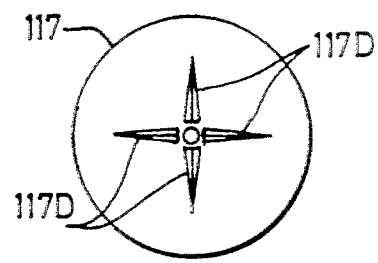

It will be appreciated that compression of the plunger head 105H can increase its stiffness thus effectiveness in flexing the latching-fingers 121 outwardly, that compression will not reduce internal diameter of the plunger 105 beyond clearance for the needle holder or hub 117 to pass it easily when a rupturable disc or membrane 136, preferably a pre-stretched film is ruptured, say by toothed rupture-aiding formations 117R on the end of the needle holder or hub 117 as shown in FIGS. 9A,B. Preferred stretched film (136) can be applied from sheet stretched in two directions, say using a suitable welding head pressed down towards a corresponding bank of upturned plungers (105). FIG. 8 also indicates a preferred indenting 105D of the plunger 105 just rearward of its head 105H, which is practical using rearward tool parts that split longitudinally and also provide flanging at 105E, and a forward end tool part for the rim of the head 105H itself that will assure no tool break lines round that sealing rim.

Figure 10:
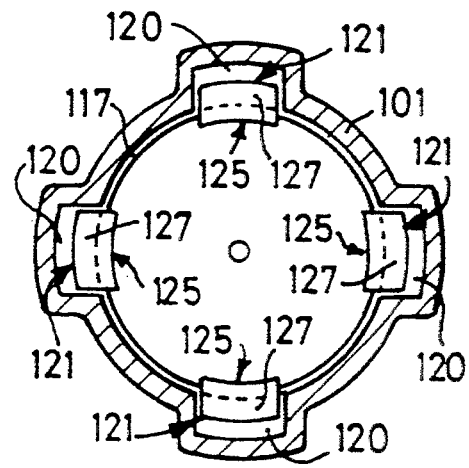
FIG. 10 is a detail transverse view concerning needle holder latching means of the body.

It will be noted that the embodiment of FIGS. 2 to 4 does not show soft infill behind the latching fingers 121, though such can be provided if desired. In fact, the body 101 is highly advantageously formed with only localised outward formations affording accommodations for flexing of the fingers 121 when spread for automatic needle retraction, see at 90° intervals and referenced 120 in FIG. 10. Suitable tooling for one-piece moulding of the body 101 will have a core part that has an outer retractable sleeve part with extensions to form the accommodations 120 and to permit both formation of the latch teeth 125 and tapered actuating surfaces 127, and core tool extraction by flexing the fingers 121 outwardly after retraction of the outer sleeve part, say using a pushed forward inner sleeve part. A particularly advantageous arrangement involving twisting during removal of the core tool forms the subject matter of a copending UK patent application.

It will also be noted that FIGS. 2 to 4 shown tapered inward formations 105F of the interior of the plunger 105, which may be fins or ribs or, and preferably, flats to grip the needle holder or hub 117 when it is forcibly retracted by action of the spring 133. As well as further assurance against any access to the needle 115 after automatic retraction, such provisions have particular value when this invention is applied to taking samples or to application of drugs etc pre-packed in cartridges as is becoming increasingly popular. For such applications, it is practical to utilise a double-ended needle and some suitable container for the sample or drug, see at 215 and 280 in FIG. 11 also showing a pierceable septum type end seal 281 for such container.

Generally, sample-taking containers (280) can be of evacuated type so that they merely needed rupturing by the inner end of the needle (215) to draw a sample from its other end already inserted into a recipient to be sampled, or can be of attachable and detachable piston type requiring piston withdrawal after such piercing by the inner end of the needle. For cartridged drugs etc, suitable containers (280) can have their own piston or piston attachment for expression after piercing by the inner end of a double-ended needle (280).

Figure 11:
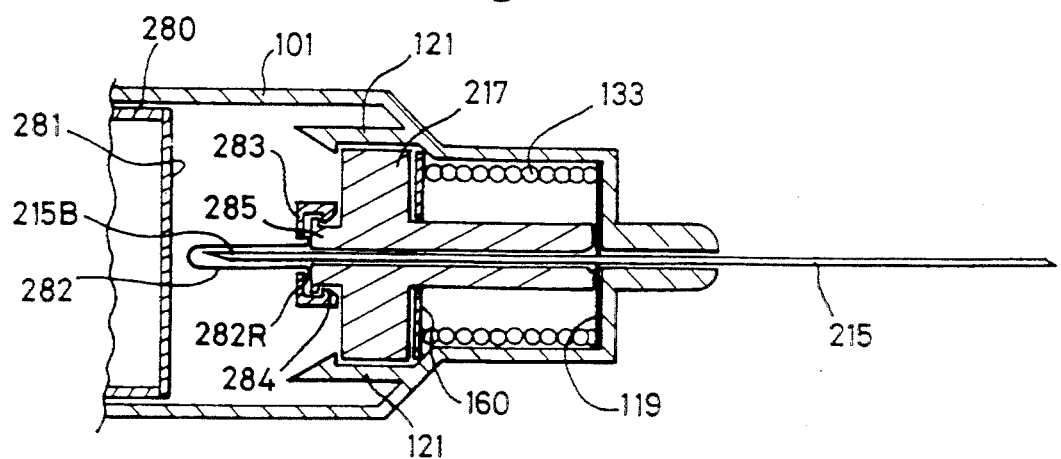
FIGS. 11 and 11A are part and detail longitudinal sectional views concerning samplers and cartridged drug dispensers.
Figure 11A:
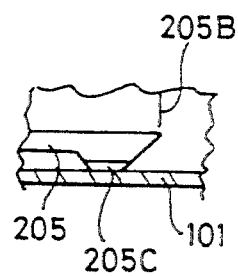

FIG. 11 shows a soft flexible cover 282 for the inner end 215B of the needle 215, which cover 282 will be pushed down and ruptured by the inner end 215B of the needle 215 when the seal 281 is ruptured as the container 280 is loaded into the body 101 or pushed into its operative state. The cover 282 has an end rim 282R shown captured by a dished apertured retainer part 282 itself shown with an inner rim 284 by which it is snap-fitted onto a headed extension formation 285 of a modified needle holder or hub 217. Other fitting for the cover 282 can be used, say by way of stretching onto a ribbed or barbed upstand of the holder or hub 217. After a container 280 has been used, it will be removed by withdrawal from the inner end of the needle 215, and a modified plunger 205 will be used for automatic retraction of the needle 215 and its related drive parts effectively just as before. Sealing of such a plunger 205 to the body 101 will not be required, see clearance formations 205C in FIG. 11A (and of which there could be many), nor will any rupturable closure of its end 205B. Such will distinguish the plunger 205 from those (5,105) for hypodermic syringes, but colour can also be used and is preferred.

However, leaving the septum disc 119 at the end of the forward or extension chamber 111 by design (spring strength and stroke relative to needle length and lubrication and/or grip of the septum disc in the forward chamber) has the advantage of the used hypodermic syringe or sampler being sealed for disposal with the needle 115 irretrievably retracted into the plunger 105 then locked to the body 101.

It has proved feasible, even for prototypes, to achieve needle stability to the extent of resisting up to 9 kilograms point loading with an operative plunger pressure of only aout 100 to 125 grams or so.

We claim:

1. In a syringe-type device that is normally sterilised before use and has a needle that is hollow for passage of contents and is automatically retractable after use, a body made from mouldable material and moulded in one piece, the body comprising a main elongate cylindrical chamber to take a plunger in slidable sealing relation therein, a forward or extension chamber extending from the main chamber beyond end of plunger movement into the main chamber and serving to house a spring to bias a holder for the needle to pass from communication with the main chamber through and beyond the forward or extension chamber, and internal latching formations for the needle holder to retain the needle holder with the spring compressed in the forward or extension chamber and biasing the needle holder for automatic retraction with the needle when the latching formations are released at end of plunger movement.

2. A syringe-type device body according to claim 1, wherein the latching formations extend in the main chamber in directions generally parallel with longitudinal axis of the body to free ends having radially inwardly directed retaining formations, the latching formations being deflectable radially outwardly in first capture and then release of said needle holder.

3. A syringe-type device body according to claim 2, wherein the latching formations have substantially no deflection from axial parallelism with in the body when in latching engagement with said needle holder.

4. A syringe-type device body according to claim 1 wherein the forward or extension chamber has a smaller section than the main chamber, and axially parallel extents of the latching formations in the main chamber are radially outward of walling of the forward or extension chamber.

5. A syringe-type device body according to claim 1 wherein each of the latching formations has a surface by which its free end is deflected radially when engaged by a cooperating surface of said plunger.

6. A syringe-type device body according to claim 1 wherein each of the latching formations is at least partially within a respective one of localised outward formations of the main chamber adjacent the forward or extension chamber.

7. A syringe-type device according to claim 1 comprising a said body and plunger construction with direct sealing between the plunger and the main chamber during sliding movement of the plunger in the body.

8. A syringe-type device according to claim 7, wherein the plunger has a hollow head with a continuous outer rim of greater nominal size than interior section of the main chamber, the main chamber and the plunger head rim permitting deformation radially of the body.

9. A syringe-type device according to claim 8, wherein the plunger head and rim and walling of the main chamber are both radially deformable, and the material of the plunger head and rim is more deformable than that of the main chamber walling.

10. A syringe-type device according to claim 1 wherein the needle has a septum disc seal that is pierced by the needle and is seated upon by the spring in the forward or extension chamber.

11. A syringe-type device according to claim 4 wherein a sealing washer between the needle holder and the spring seats and seals between the needle holder and entry from the main chamber to the forward or extension chamber.

12. A syringe-type device according to claim 1 wherein the needle and its holder are installed in the body during manufacture of the device by assembly together with retraction drive parts including the spring and any seals in a guide member that is slidable in the main chamber to bring said assembly into registration with entry to the forward or extension chamber, the assembly then being pushed off the guide member and into the forward or extension chamber with accompanying compression of the spring until there is latching engagement of the needle holder by the latching formations.

13. A syringe-type device according to claim 4 wherein the plunger is hollow to accommodate the needle and its holder and any retraction drive parts that move therewith, and is initially sealed at its end nearest the forward or extension chamber by a rupturable closure member that is ruptured by engagement with the inner end of the needle and its holder.

14. A syringe-type device according to claim 13, wherein the closure member is a pre-stretched film secured across the end of the plunger.

15. A syringe-type device according to claim 13, wherein the needle holder has formations aiding rupture of the rupturable closure member.

16. A syringe-type device according to claim 13, wherein the plunger has interior tapering formations to slow, stop and grip the needle holder in spring-driven automatic retraction.

17. A syringe-type device according to claim 1 wherein the body has formations to cooperate with plunger formations after automatic retraction so as to latch the plunger in the body.

18. A syringe-type device according to claim 17, further comprising a removable spacer between free ends of the body and its plunger, the spacer serving to prevent engagement of the formations by which the plunger is latched on the body.

19. A syringe-type device according to claim 18, wherein the spacer is of folded sheet material that is further folded over and adhered to the free end of the plunger and flanging of the free end of the body.

20. A syringe-type device according to claim 18, wherein the spacer carries at least a tell-tale for sterilisation having taken place.

21. A syringe-type device according to claim 1 wherein, prior to sterilisation, combined testing and needle lubrication is done by piercing a septum seal to a blind pressure test cell, the septum seal carrying lubricant for the needle.

22. A syringe-type device according to claim 1 and for use with a container insertable into the body, wherein the needle is double-ended and its inward end serves to pierce a seal of the container.

23. A syringe-type device according to claim 22, wherein, after the container is later removed, a plunger is used to release the latching provisions, which plunger does not make a seal to interior of the main chamber.

24. A syringe-type device according to claim 23, wherein the last-mentioned plunger has an open end to receive the needle and its holder.

25. A syringe comprising:
a body, said body including a longitudinally extending hollow portion defining an interior chamber open at a first end, said body including a surface formed at a second end of the chamber, said surface having a needle opening formed therethrough, said surface closing the second end except for said needle opening, said body further including at least two deflectable latch fingers extending into said chamber from said surface, said body formed of a mouldable material and moulded in one piece with said hollow portion, said surface and said latch fingers integrally formed as a unitary structure;
a plunger slidably disposed within said chamber through the open first end;
a needle holder disposed with the interior chamber adjacent said surface, said needle holder holding a hollow needle fixed thereto, said needle extending through the needle opening;
a spring disposed between at least a portion of said needle holder and said surface, said spring compressed by said needle holder such that said spring provides a force which acts so as to urge said needle holder towards said first end of said chamber, wherein,
said latch fingers include a portion which act to hold said needle holder and said needle in position against the urging of said spring, and wherein, when said plunger is slid forwardly in said chamber and into contact with said fingers, said fingers are flexed radially outwardly so as to allow said needle holder and said needle to be retracted within said chamber by the urging of said spring.

* * * * *